United States Patent [19]

Zale

[11] Patent Number: 5,362,859

[45] Date of Patent: Nov. 8, 1994

[54] HIGH-CAPACITY AFFINITY SUPPORTS AND METHODS FOR THE PREPARATION AND USE OF SAME

[75] Inventor: Stephen E. Zale, Uxbridge, Mass.

[73] Assignee: Sepracor, Inc., Marlboro, Mass.

[21] Appl. No.: 920,240

[22] Filed: Jul. 27, 1992

[51] Int. Cl.$^5$ .................. C07K 3/20; C07K 17/08; C07K 17/12; C08G 63/91

[52] U.S. Cl. .................. 530/413; 530/350; 530/387.1; 530/390.1; 530/390.5; 530/405; 530/412; 530/810; 530/811; 530/812; 530/813; 530/814; 530/815; 530/816; 525/54.1

[58] Field of Search ............ 530/387.1, 390.1, 390.5, 530/405, 350, 810, 814, 412, 811, 815, 812, 816, 413, 813; 525/54.1; 514/12

[56] References Cited

PUBLICATIONS

Weber and Bailon, "Application of receptor-affinity chromatography to bioaffinity purification", *Journal of Chromatography* 510: 59–69 (1990).

Narayanan et al., "Preparative affinity chromatography of proteins—Influence of the physical properties of the base matrix", *Journal of Chromatography* 503: 93–102 (1990).

Nakamura et al., "Tresyl-activated support for high-performance affinity chromatography", *Journal of Chromatography* 510: 101–113 (1990).

Comoglio et al., "Factors affecting the properties of insolubilized antibodies", *Biochimica et Biophysica Acta* 420: 246–257 (1976).

Tharaken et al., "Effect of feed flow-rate, antigen concentration and antibody density on immunoaffinity purification of coagulation factor IX", *Journal of Chromatography* 552: 153–162 (1990).

Primary Examiner—Christina Y. Chan
Attorney, Agent, or Firm—Kriegsman & Kriegsman

[57] ABSTRACT

An affinity support having an improved capacity for binding target compounds. The support includes an immobilized modified ligand of increased molecular weight. The molecular weight of the ligand is increased via the action of condensation reagents or crosslinkers prior to immobilization. The affinity support is useful in affinity separations of proteins and other biomolecules from complex, biologically-derived fluids.

20 Claims, 1 Drawing Sheet

HIGH-CAPACITY AFFINITY SUPPORTS AND METHODS FOR THE PREPARATION AND USE OF SAME

TABLE OF CONTENTS

1. FIELD OF THE INVENTION
2. BACKGROUND OF THE INVENTION
3. BRIEF DESCRIPTION OF THE DRAWINGS
4. SUMMARY OF THE INVENTION
5. DETAILED DESCRIPTION OF THE INVENTION
6. EXAMPLES
   6.1. EXAMPLE 1
      6.1.1. REACTION OF PROTEIN G LIGAND WITH WATER-SOLUBLE CARBODIIMIDE TO INCREASE MOLECULAR WEIGHT
      6.1.2. IMMOBILIZATION OF EDC-MODIFIED PROTEIN G ON ACTIVATED HOLLOW FIBER MEMBRANES
      6.1.3. DETERMINATION OF THE AMOUNT OF IMMOBILIZED PROTEIN G
      6.1.4. DETERMINATION OF TARGET PROTEIN BINDING CAPACITY
   6.2. EXAMPLE 2
   6.3. EXAMPLE 3
   6.4. EXAMPLE 4
   6.5. EXAMPLE 5
   6.6. EXAMPLE 6
   6.7. EXAMPLE 7
   6.8. EXAMPLE 8
   6.9. EXAMPLE 9
   6.10. EXAMPLE 10

1. FIELD OF THE INVENTION

The invention generally relates to improved support materials for binding selected compounds thereto in the practice of affinity chromatography. The invention particularly relates to solid support materials which have high molecular weight ligand proteins immobilized thereupon for binding target proteins to the support.

2. BACKGROUND OF THE INVENTION

Affinity purification ("affinity chromatography") broadly refers to separation methods based on the relatively high binding capacity ("affinity") of a target material to be purified, generally termed a "ligate," for a complementary ligand. Affinity separation is a preferred method for purifying proteins and other biomolecules from complex, biologically derived fluids. The key to the method's attractiveness is its unequaled degree of selectivity.

Affinity separations, as they are conventionally practiced, typically involve a number of sequential steps. First, a solution containing a component to be separated from the solution (a component of interest) is passed through a column containing a highly specific ligand immobilized on a support, usually a membrane or high-surface-area beads or particles. As the fluid passes through the column in this loading step, the desired component binds selectively and reversibly to the immobilized ligand, while most impurities pass unhindered. Residual impurities are removed by flushing the column with an appropriate buffer solution in a subsequent washing step. The component, now purified but still bound to the immobilized ligand, is then recovered by passing an eluent solution through the column that has the effect of disrupting the ligand-to-ligate binding interaction. Generally, the pH, concentration of a salt, or some other chemical characteristic of this eluent solution is altered significantly from the corresponding values of the loading and wash solutions, and it is this change that is responsible for weakening the affinity interaction and thereby causing desorption and elution of the ligate molecule.

Numerous products and procedures have been developed for the preparation of solid membrane and particle-based affinity supports to retain immobilized protein ligands for separations. See, "Affinity Chromatography: Principles and Methods," Pharmacia LKB Biotechnology, 1988; Scouten, W. H. "Affinity Chromatography: Biospecific Adsorption on Inert Matrices," Wiley Interscience, 1981; and "Methods in Enzymology," Vol- XXXIV, Affinity Techniques, Jacoby, W. B. and Wilchek, M., Eds., Academic Press, 1974. Important parameters for these products and procedures include: (i) the maximum amount of ligand that can be immobilized on the affinity support, (ii) the percent yield with which the ligand can be immobilized, and (iii) the degree to which the functionality of the ligand (i.e., the ability of the ligand to bind target proteins to the ligand) is preserved once the ligand has been immobilized. All of these influence the binding capacity of the affinity support and the cost of preparing it.

The literature also describes various approaches to increasing the ligand binding capacity and efficiency while preserving ligand biological function. See for example, D. Weber et al, *J. Chromatography*, 510, 59–69 (1990). These approaches include: (i) varying the amount and type of the functional groups present on the support, (ii) optimizing the conditions of pH and ionic strength for attaching the ligand molecule to the support, and (iii) so called "site-directed" methods which aim to bind the ligand molecule to the support at a site on the ligand that is not involved in interaction with the target protein molecule. All of these approaches, however, are subject, among others, to the following limitations:

1. The maximum amount of ligand protein that can be bound onto a porous support is a function of the surface area on the support available for the functional groups, with higher surface area support matrices generally having more functional groups and normally binding more ligand. High surface area is usually achieved by decreasing the pore size of the support matrix. If the pore size is decreased beyond an optimum value, however, exclusion of either the ligand or the target protein will occur and the capacity of the matrix will be adversely affected. See, Narayanan, S. R., et al., *J. Chromatography*, 503, 93–102 (1990).

2. As the amount of ligand presented during immobilization to the support matrix approaches the maximum ligand binding capacity of the support, the efficiency of immobilization begins to decrease. Therefore, it becomes costlier in terms of wasted ligand to produce supports that contain approximately the maximum amount of ligand that can be bound. See, e.g., Nakamura, K., et al., *J. Chromatography*, 510, 101–113 (1990).

3. As the density of ligand protein on the support is increased, the target protein binding capacity per gram of immobilized ligand begins to decrease, presumably due to steric factors that reduce the accessibility of the target protein molecules to the binding sites on the immobilized ligand. See, e.g., Comoglio, S., et al., *Biochem. Biophys. Acta*, 420, 246-257 (1976) and Tharakan, J. P., et al., *J. Chromatography*, 522, 153-162 (1990).

A need therefore exists for methods to immobilize protein ligands, providing an increase in the maximum amount of ligand that can be immobilized on the support without appreciable loss of biological function of the ligand, i.e., without loss of its target protein binding capacity. This would enable production of higher capacity affinity supports as well as more efficient and less costly production of affinity supports.

3. BRIEF DESCRIPTION OF THE DRAWINGS

4. SUMMARY OF THE INVENTION

Figure 1:
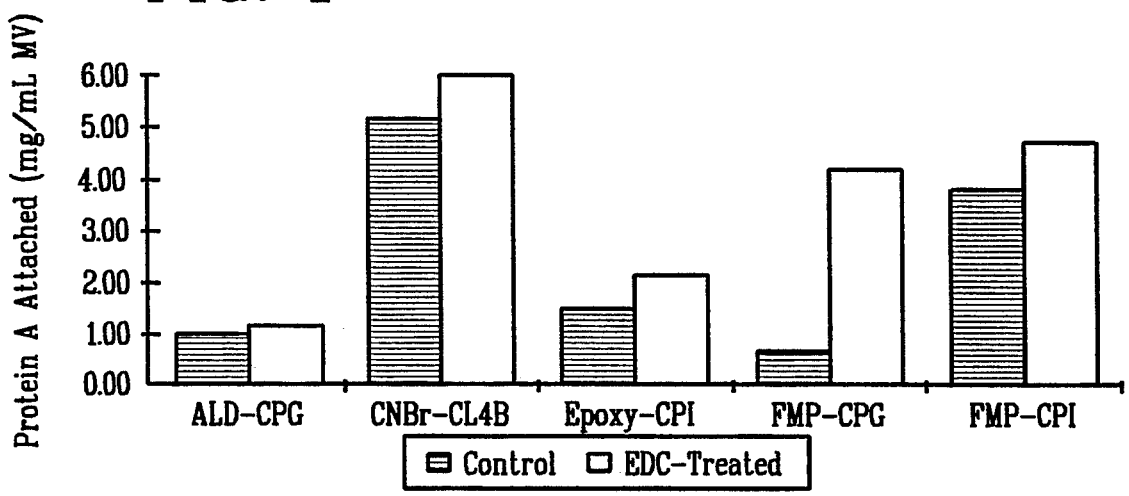
FIG. 1 shows the effect on the amount of Protein A attached to activated support materials when the Protein A is treated with 1-ethyl-3-(3-dimethylaminopropyl)-carbodiimide (EDC). The experiments designated ALD-CPG, CNBr-CL4B, Epoxy-CPI, FMP-CPG, and FMP-CPI correspond to Examples 6, 7, 8, 9, and 10, respectively.

In accordance with the present invention, a new method is provided for the immobilization of increased amounts of ligands having a selective and reversible binding affinity for a target compound onto solid supports. The resulting affinity supports have an increased capacity for separating and binding a variety of target compounds including proteins from a mixture of compounds.

The method of the present invention comprises the chemical modification of the desired ligand to increase the molecular weight of the ligand prior to the immobilization of the modified ligand onto the solid support material. The molecular weight of the ligand is increased via the action of chemical reagents, such as condensation reagents or crosslinking reagents, prior to contacting the ligand with the solid support. While not wishing to be limited by theory, it is believed that modified ligand having an increased molecular weight may be in the form of an oligomer of two or more individual ligands or a covalent aggregate of same. Regardless of the exact form of the modified ligand, it has been discovered surprisingly that a greater amount of the modified ligand can be immobilized onto the solid support material relative to the amount that can be bound to the same solid support material using unmodified individual ligands.

Preferred ligands whose molecular weights may be increased according to the present invention include Fc-specific immunoglobulin-binding proteins such as Protein A, Protein G, and hybrids thereof, including hybrids of Proteins A and G; antibodies; receptors; lectins; and enzymes. The affinity supports of the invention are made by contacting the solid support material with the increased-molecular-weight ligand to immobilize the ligand onto the support material.

The improved affinity supports of the invention, when employed in affinity separations of mixtures that include compounds such as proteins, provide surprisingly improved separation yields of target molecules from those mixtures. In accordance with the invention the amount of ligand immobilized onto the support, the efficiency of ligand immobilization, and the target protein binding capacity of the resulting support all are surprisingly greater than can be achieved by prior art methods.

Thus, it is an object of the present invention to provide an affinity support having an increased capacity for binding a target compound during affinity separations comprising (a) a solid support material having a surface that can accommodate the immobilization of molecules of a ligand, such as an Fc-specific immunoglobulin-binding protein ligand; and (b) a modified ligand immobilized on the surface of the solid support material, the modified ligand being comprised of a plurality of ligand molecules covalently bound to one another prior to immobilization of the modified ligand on the support, such that the modified ligand (i) has a molecular weight that is greater than that of an individual ligand molecule, and (ii) exhibits a selective and reversible binding affinity for the target compound.

In particular embodiments of the present invention the affinity support is derived from a solid support material that may include a porous or nonporous particle or a porous membrane. Preferably, the particle or membrane further comprises agarose, polyethersulfone, polystyrene, silica, celluloses, poly-trisacryl, poly-metatrisacryl, controlled pore glass, dextran, polyamides, polyacrylamide, hydroxyalkylmethacrylate gels, polyacrylamide/agarose gels, ethylene copolymers, diol-bonded silica, copolymers of methacrylamide, methylene bismethacrylamide, glycidyl-methacrylate, allyl-glycidylether, polyethersulfone coated with hydroxy ethyl cellulose, and polymer-silica composites. Most preferably, the particle or membrane further comprises a material selected from the group consisting of a polymer-silica composite or a polyethersulfone coated with hydroxyethylcellulose.

In accordance with the present invention, the surface of the solid support material is preferably treated with an activation agent, prior to immobilization of the modified ligand. Supports can be activated with epoxy, fluoro-methylpyridinium p-toluenesulfonate, cyanogen bromide, triazine, carbonyl diimidazole, N-hydroxysuccinimide, aldehyde or hydrazide functionalities, and the like.

It is likewise an object of the present invention to provide a modified ligand derived from an $F_c$-specific immunoglobulin-binding protein, such as Protein A, Protein G, or hybrids thereof. In one embodiment of the present invention, the modified ligand comprises an oligomer of two or more Fc-specific immunoglobulin-binding proteins. In another embodiment, the modified ligand comprises a covalent aggregate of two or more Fc-specific immunoglobulin-binding proteins.

Thus, in the present invention, a modified ligand is provided in which a plurality of ligand molecules is covalently bound to one another by the action of a condensation or crosslinking reagent. Preferably, the reagent is selected from the group consisting of carbodiimides, dialdehydes, bifunctional imidoesters, m-maleimidobenzoyl-N-hydroxysuccinimide ester, m-maleimidobenzoyl-N-hydroxysulfosuccinimide ester, and 2-ethyl-5-phenylisoxazolium-3'-sulfonate.

In a preferred embodiment of the present invention, an affinity support having an increased capacity for binding a target compound, preferably an immunoglobulin, during affinity separations comprises: (a) a solid support material comprising a polyethersulfone and having a surface (i) coated with hydroxyethylcellulose, and (ii) activated with fluoromethylpyridinium p-toluenesulfonate to accommodate the immobilization of molecules of a ligand, in particular, molecules of an Fc-specific immunoglobulin-binding protein ligand; and (b) a modified ligand immobilized on the surface of the solid support material, the modified ligand being comprised of a plurality of ligand molecules covalently bound to one another prior to immobilization of the modified ligand on the support, by the action of ethyl-3-(3-dimethylaminopropyl)-carbodiimide such that the modified ligand (i) has a molecular weight that is greater than that of an individual ligand molecule, and (ii) exhibits a selective and reversible binding affinity for the target compound. As stated previously, the ligand is most preferably selected from the group consisting of Protein A, Protein G, or hybrids thereof.

In yet another object of the present invention, a method is provided for making an affinity support having an increased capacity for binding a target compound during affinity separations of the target compound from a mixture of compounds, comprising chemically treating molecules of an Fc-specific immunoglobulin-binding protein ligand to form a modified ligand comprised of a plurality of ligand molecules covalently bound to one another, and subsequently immobilizing the modified ligand onto the surface of a solid support material, such that the modified ligand (i) has a molecular weight that is greater than that of an individual ligand molecule, and (ii) exhibits a selective and reversible binding affinity for the target compound.

In specific embodiments of the present invention, the immobilization of the modified ligand is effected by adsorption thereof onto the support material. Yet in others, the immobilization of the modified ligand is effected by treating the solid support material with an activation agent and contacting the modified ligand with the solid support material.

In accordance with the objectives of the present invention, the chemical modification of the ligand may be effected by treatment of the ligand with a condensation or crosslinking reagent, including, but not limited to, carbodiimides, dialdehydes, bifunctional imidoesters, m-maleimidobenzoyl-N-hydroxysuccinimide ester, m-maleimidobenzoyl-N-hydroxysulfosuccinimide ester, and 2-ethyl-5-phenylisoxazolium-3'-sulfonate.

Moreover, a wide variety of ligands exhibiting a selective and reversible binding affinity for a target compound can be utilized, including, but not limited to, Fc-specific immunoglobulin-binding proteins, enzymes, antibodies, receptors and lectins.

In preferred embodiments of the present invention, the solid support may be in the form of a particle or a membrane. Most preferably, the particle or membrane further comprises a polymer-silica composite or a polyethersulfone coated with hydroxyethylcellulose.

Thus, it is an object of the present invention to provide a method of making an affinity support having an increased capacity for binding a target compound during affinity separations of the target compound from a mixture of compounds, comprising chemically modifying molecules of an Fc-specific immunoglobulin-binding protein ligand by treating the ligand molecules with ethyl-3-(3-dimethylaminopropyl)carbodiimide to form a modified ligand comprised of a plurality of ligand molecules covalently bound to one another, activating the surface of a polyethersulfone solid support material coated with hydroxyethylcellulose by treating the solid support material with fluoro-methylpyridinium p-toluenesulfonate, and subsequently immobilizing the modified ligand onto the surface of the activated solid support material, such that the modified ligand (i) has a molecular weight that is greater than that of an individual ligand molecule, and (ii) exhibits a selective and reversible binding affinity for the target compound.

In a further object of the present invention, a method is provided whereby affinity separations can be performed with increased yields of a target compound. Such method comprises: (a) contacting a mixture of compounds with an affinity support formed by chemically treating molecules of an Fc-specific immunoglobulin-binding protein ligand to form a modified ligand comprised of a plurality of ligand molecules covalently bound to one another, and subsequently immobilizing the modified ligand onto the surface of a solid support material, such that the modified ligand (i) has a molecular weight that is greater than that of an individual ligand molecule, and (ii) exhibits a selective and reversible binding affinity for the target compound; and (b) maintaining contact between the mixture and the affinity support for a time sufficient to selectively and reversibly bind the target compound to the immobilized modified ligand, thereby separating the target compound from the mixture. In preferred methods of the present invention, the target compound comprises an immunoglobulin. Most preferably, the target compound is IgA, IgG, IgM or mixtures thereof.

These and other objects of the present invention will be apparent to those of ordinary skill in the art from the present disclosure and, in particular, from the detailed description and specific embodiments described below.

5. DETAILED DESCRIPTION OF THE INVENTION

In a preferred embodiment of the present invention, the molecular weight of a ligand is increased prior to immobilization of the ligand on an affinity support. The molecular weight of the ligand is increased via chemical modification by a variety of reagents, including condensation reagents or crosslinking reagents. This embodiment of the invention comprises two distinct steps: (i) chemically modifying the ligand to increase its molecular weight, and (ii) immobilizing the resulting high molecular weight ligand on an affinity support.

In the chemical modification step, the molecular weight of the ligand is increased by allowing the ligand to react either with a crosslinker or a condensation reagent. This "oligomerization" reaction normally yields a distribution of oligomers or covalent aggregates as dimers, trimers and higher molecular weight complexes. The nature of the distribution, and hence, the characteristics of the support derived from the preparation, depends, inter alia, on the type and amount of crosslinker or condensation reagent, on the ligand concentration, and on the presence or absence of additional substances such as polymers that may participate in the crosslinking or condensation reactions. These additional substances may participate in the crosslinking or condensation reactions, but need not participate directly in binding of the target compound.

In the immobilization step, the reaction mixture of modified, high molecular weight ligand is contacted with a solid support to immobilize the ligand on the support. The support surface may contain activated functional groups to facilitate immobilization of the ligand. Alternatively, if the support surface is not treated with an activating agent, the immobilization may be of a noncovalent nature, e.g., by adsorption. In this step, the reaction mixture immediately can be applied to the support after appropriate dilution and pH adjustment. Alternatively, the reaction mixture first can be dialyzed to remove low molecular weight components prior to the immobilization step. After immobilization is completed, the support is washed to remove unbound or loosely bound ligand.

In accordance with the invention, increasing the molecular weight of the ligand surprisingly provides increased efficiency of ligand immobilization as well as an increase in the maximum amount of ligand which can be immobilized onto the support. Surprisingly, the capacity of the support to bind a target molecule is also greatly increased. Indeed, the immobilized modified ligands of the present invention display little or no loss of biological function as compared with ligands whose molecular weights have not been so increased.

The invention can be employed with many types of ligands. Useful ligands include Fc-specific immunoglobulin-binding proteins such as Protein A, Protein G, and hybrids thereof, including hybrids of Proteins A and G; receptor proteins which bind human interleukins, growth factors, interferons, hemopoietic factors and the like; lectins such as lentil lectin, concanavalin A, and wheat germ lectin; enzymes; and antibodies such as monoclonal or polyclonal antibodies or fragments thereof derived from mammals, e.g., mouse, sheep, goat or rabbit which have binding specificity to antigens. Examples of antigens include human coagulation factor VIII, factor IX, protein C; human growth hormone, erythropoietin, colony stimulating factor, macrophage colony stimulating factor, granulocyte colony stimulating factor, and the like. The invention also may be employed to bind small molecules including dyes such as cibachron blue, procion red, basilein blue and the like, amino acids, ion exchange functionalities, or enzyme inhibitors such as arginine, benzamidine, lysine and the like to polymers such as polylysine, polyglutamic acid, polyethyleneimine and the like by the first step of chemical modification followed by immobilizing the polymer bearing the dye or enzyme inhibitor onto the support.

The oligomerized ligands of the invention are at least dimers. The oligomers, however, do not have a molecular weight that is so high as to cause precipitation of the ligand from the solution employed. The oligomerized ligands, which are capable of binding the target molecules to the support, are produced by contacting the ligand monomer with suitable reagents or crosslinkers. Preferably, the ligand monomers are oligomerized by treating with 1-ethyl-3-(3-dimethylaminopropyl)-carbodiimide (EDC). Condensation reagents other than EDC that mediate formation of linkages between functional groups present on the ligand molecules also can be used to oligomerize ligands in the invention. Examples of suitable reagents include but are not limited to dialdehydes such as glutaraldehyde, bifunctional imidoesters such as dimethyl suberimidate, carbodiimides such as N,N'-dicyclohexylcarbodiide, and 2-ethyl-5-phenylisoxazolium-3'-sulfonate, and heterobifunctional crosslinking agents such as m-maleimidobenzoyl-N-hydroxysuccinimide ester and m-maleimidobenzoyl-N-hydroxysulfosuccinimide ester.

As is known in the art, supports useful for ligand immobilization typically have a large surface area and comprise an open and loose porous network to maximize interaction of surface-bound ligand with ligate during the separation procedure. The support surface is chemically and biologically inert toward at least the ligand and the ligate target compound. The surface also is stable under the reaction conditions employed, for example during surface activation, ligand binding, and ligand-ligate complex formation and dissociation (i.e., elution), especially with respect to the solvent, pH, salt, and temperature conditions employed. The surface also should be stable for a reasonable length of time under ordinary storage conditions. To minimize competition for the target material and to maximize purity of recovered product, the supports for immobilization of the high molecular weight ligands, especially biospecific ligands, are free from extraneous ion exchange sites and do not promote non-specific bonding. Support surfaces, especially those used in pressurized affinity separation techniques, also should be mechanically strong and be able to withstand at least the moderate pressures, such as 5 bar, typical of these conventional systems. Further, since the surfaces are frequently derivatized, for example to promote ligand immobilization or to permit improved ligand/target molecule interaction, the surface should be readily derivatizable to these ends, preferably at room temperature and in aqueous media, without the use of toxic chemicals.

The affinity support materials of the invention may be employed in the form of porous or nonporous particles or membranes. The membranes, particularly, microporous membranes, may be configured as hollow fibers or flat sheets. Useful affinity support materials include, but are not limited to, agarose gels; polyethersulfone; polystyrene; silica; polytrisacryl; poly-meta-trisacryl; controlled pore glass (CPG), celluloses such as hydroxymethyl or hydroxyethyl cellulose; dextran; polyamides such as nylons; polyacrylamide; hydroxyalkylmethacrylate gels; polyacrylamide/agarose gels; ethylene copolymers, especially with polyvinyl acetate; copolymers of methacrylamide, methylene bis-methacrylamide, glycidyl-methacrylate and/or allyl-glycidyl-ether such as Eupergit C from Rohm Pharma, Darmstadt, West Germany; and diol-bonded silica. Composite supports may also be used, such as porous polyethersulfone coated with hydroxyethylcellulose, polymer-silica composites prepared by in situ polymerization of monomers possessing a polymerizable double bond with crosslinkers having at least two polymerizable double bonds, and the like.

Generally, this invention can be performed using any type of attachment chemistry suitable for immobilizing the oligomerized ligands onto the support matrix. Examples of useful attachment chemistries include, but are not limited to, coupling to supports activated with epoxy, fluoromethyl-pyridinium p-toluenesulfonate (FMP), cyanogen bromide, triazine, carbonyl diimidazole, N-hydroxysuccinimide, or aldehyde or hydrazide functionalities.

The affinity supports of the invention which bear increased-molecular-weight ligands are especially suitable for separation of biological materials, particularly proteins, and especially for recovery or removal of selected blood proteins such as pathological antigens or antibodies.

In one embodiment of the invention, ligand Protein A or Protein G molecules are treated with EDC to provide increased-molecular-weight ligand oligomers which then are immobilized on hollow fiber membrane modules activated with FMP. The resulting fiber modules show surprisingly higher IgG capacities than modules prepared by immobilization with untreated Protein A or Protein G ligands.

The increased capacities of the hollow fiber modules prepared according to this embodiment provide surprisingly increased productivity, increased product concentration and more efficient buffer consumption when employed in applications such as affinity separations to purify monoclonal and polyclonal antibodies from crude mixtures such as cell culture supernatant, serum or ascites fluid. Use of such modules thereby improves the economics of antibody purification.

The invention is now further described with reference to the following, non-limiting examples. Unless otherwise defined, all temperatures are in ° C. and all percentages are in parts by weight.

6. EXAMPLES

6.1. EXAMPLE 1

6.1.1. Reaction of Protein G Ligand with Water-soluble Carbodiimide to Increase Molecular Weight A stock solution of 40 mg/ml of recombinant Protein G ligand (Gammabind Type II supplied by Genex Inc.) in water is diluted with distilled water to a concentration of 10 mg/ml by adding 1.1 ml of the stock solution to 3.3 ml water. One milliliter portions of the diluted solution are added to each of four test tubes and the pH of each portion is adjusted to pH 4.5 by addition of 0.2 ml of 0.6 M 2-[N-morpholino]ethanesulfonic (MES) acid buffer pH 4.5. (This 0.6 M MES buffer is prepared by dissolution of 31.95 g MES·$H_2O$ (Sigma) in 250 mL water followed by adjustment of the pH to 4.5 with 3 M NaOH.)

A solution of 20 mg/ml of EDC from Pierce Chemical Co., in 0.1 M MES buffer pH 4.5, is prepared. The 0.1 M MES buffer is prepared by performing a six-fold dilution of the above-mentioned 0.6 M MES buffer with water. The solution of EDC in the 0.1 M MES buffer is added to each of the test tubes in varying amounts as listed below in Table I:

TABLE 1

| Sample | μL EDC | mg EDC per mg Protein G |
|---|---|---|
| 1 | 0 | 0 |
| 2 | 10 | 0.02 |
| 3 | 25 | 0.05 |
| 4 | 50 | 0.1 |

The sample test tubes are incubated at room temperature on a rotary shaker for two hours. To each sample is then added 4.8 mL of the above-mentioned 0.1 M MES buffer to yield a final protein G ligand concentration of 1.7 mg/ml.

The resulting reaction mixtures are analyzed by SDS-PAGE under reducing conditions. Protein bands are visualized by staining with Coomassie blue. The bulk of the protein G ligand in Sample 1 (which did not include EDC) migrated with an apparent molecular weight of approximately 40,000. This is in accordance with previous studies on the migration of Protein G on SDS gels. See, Sjobring, A. et al., *J. Biological Chemistry*, 266, 399–405 (1991). In samples 2–4 of Table I, however, increasing the amount of EDC resulted in a gradual decrease in intensity of the protein band that corresponds to native Protein G. Increasing the amount of EDC also caused appearance of protein bands corresponding to ligands with apparent molecular weights from approximately 55,000 to more than 180,000. The fraction of protein G ligand that exhibits higher molecular weight also increased with greater amounts of EDC. In addition, the distribution of high molecular weight Protein G ligand reaction products shifted toward higher molecular weights as the amount of EDC was increased.

6.1.2. Immobilization of EDC-modified Protein G on Activated Hollow Fiber Membranes The high molecular weight protein G ligand reaction products generated above are attached to hollow polyether sulfone (PES) fiber support membranes, the surfaces of which have been coated with hydroxyethylcellulose and then activated with FMP as discussed below. The activated fiber support membranes are prepared in the following manner: PES, which is also known as Victrex (by ICI America, grade 5200P, obtained in 15 kg bags), is dried in an oven at 150° C. for 3 h and then allowed to cool to 60° C. for several hours more. The total time of heating in the oven is not less than about 24 h. PEO (Polyox 301, MW 4000 kD, by Union Carbide Corp., obtained in 140 lb drums) is pretreated in a vacuum oven at room temperature for about 124 h. Care is taken not to leave the pretreated polymers in the open air for extended periods before adding them to the mixer.

Both NMP (i.e., N-Pyrol, Cat. No. 1-3-72755/000 & 5-72, by GAF Chemicals Corp., obtained in 55 gal drums) and glycerin (by Baxter Scientific Product Group, Mallincrodt, catalog #5092-4, analytical Reagent) are used as received, but precautions are taken to minimize the uptake of atmospheric moisture by adding them to the mixer immediately after removal from the respective containers. The containers should be closed tightly when they are not in use.

NMP (2812 g) and glycerin (1128 g) are pre-mixed in a 1 gal container before adding them to a Ross (model PVM2) mixer at room temperature. The Ross mixer is fitted with a source for purging with nitrogen. The inert atmosphere is maintained over all liquids until the PEO has been added. On applying pre-mixed NMP/glycerin to the Ross mixer, two of the mixing blades are started: the anchor blade at 135 rpm, and the disperser blade at 3,500 rpm. PEO (360 g) is added while mixing at room temperature over the period of about one minute. A 500 gram portion of NMP is then added to make a total of 3312 gram NMP in the dope. At this point the disperser blade is switched off and Mokon heat exchange unit is set at 120° c. After 3 h of mixing, the PES (1200 g) is added over the space of 2–3 minutes, and the temperature is noted with the anchor blade maintained at 135 rpm. After an additional 18 h, a steady decrease in temperature is initiated by setting the Mokon at 60° c. Within about 1.5 h of making this temperature change, the dope usually attains a temperature of about 75±5° C., at which time a vacuum is gradually applied to de-gas the mixture. Full vacuum is usually achieved within 15 min and is maintained for a further 5 min. The mixer is then switched off while continuing to de-gas. A vacuum is maintained for 1–2 min longer before introducing nitrogen to re-establish atmospheric pressure in the mixing vessel at 60° C.

a dope as prepared above is extruded through a double annular co-extrusion spinnerette. Spinnerette temperature is maintained at 80° C. throughout the duration of the experiment. Other fixed parameters preferably include:

dope pump speed—about 70 rpm
quench bath temperature—about 90° C.
quench bath composition—Deionized (DI) water intraanular fluid composition—about 70% NMP: 30% DI water (v/v)

extraanular fluid composition—about 70% NMP: 30% DI water (v/v)

intraanular fluid flow rate—about 30.2 (±1.2) ml/min.

first and second godet bath temperatures—about 42.5 (±2.5)° C.

Other parameters which may also be varied are: air gap or spinnerette height above the quench bath (which results in a change in fiber take-up rate or the rate of fiber production in linear feet per minute) and extraannular fluid flow rate. The latter is varied from zero to 66 mL/min with spinnerette heights ranging from 3–7 inches. Note that the spin line contains only two godet baths. A very pronounced dependence of membrane hydraulic permeability (Lp) for DI water on extraanular fluid flow rate is seen to exist as a fiber with zero outer annular fluid flow is seen to be equivalent to a fiber produced with a conventional tube-in-orifice spinnerette.

A fiber sample having an LP of $337 \times 10^{-9}$ mL/min and an air gap of 2.5 inches. The sample has an ID of 950 μm and an OD of 1500 μm. When observed by electron microscopy, the fiber sample is seen to have pores of 1–3 μm on two surfaces. Overall pore size distribution in the matrix of the approximately 300 μm fiber wall varies within the range of about 1–2 orders of magnitude, but the great majority of the pores are within 1 order of magnitude of each other in size. These results indicate that this membrane is an example of a substantially skinless relatively isotropic microporous membrane.

The PES/PEO hollow fiber membrane sample prepared above is autoclaved with steam at 121° C. for 15 min and then treated with 5 N NaOH at 95° C. for 16 h. The membrane sample is then allowed to react with an 0.1 N NaOH solution containing 10 wt % ethylene glycol diglycidyl ether (EGDGE) at room temperature for 4 h. The membrane is then isolated and preferably washed with fresh cold water to fully remove unreacted EGDGE and excess base. Next, the sample is immersed in a 0.6 N NaOH solution containing 2 wt % hydroxyethyl cellulose (HEC), Natrosol 25 JR, Aqualon Company, Wilmington, Del., USA) and heated to 60° C. for 16 h. Afterwards, the sample is rinsed in 60° C. H₂O to remove unbound components. The resulting material is referred to as 1X HEC. The 1X HEC material is treated sequentially with EGDGE, fresh cold water, HEC, and fresh hot water, as described above, to give a material referred to as 2X HEC.

2X HEC made in the manner described above is treated with an acetonitrile solution containing 2 wt % of 2-fluoro-1-methylpyridinium p-toluenesulfonate (FMP, Aldrich Chemical Co., USA) and 1 wt. % triethylamine at room temperature for 15 min. The treated sample is then washed with fresh acetonitrile and then washed with 5 mM aqueous hydrochloric acid. Next, the membrane is air dried at room temperature. Aliquots (0.80 mL) of each of the four mixtures of samples 1–4 in Table 1 are diluted with 3.2 ml of 0.03 M sodium bicarbonate and added to a 15 mL conical centrifuge tube that contains five 2-cm segments of the activated hollow fiber membrane. The tubes are incubated overnight (16 hours) at 30° C. on a rotary shaker to bind the protein to the support.

The tubes containing the fiber membrane samples are taken from the incubator, and residual unbound ligand protein is removed. Residual unreacted FMP groups are deactivated by incubating the membranes in 4.0 mL of 0.1 M sodium carbonate, pH 11.3, for 2 hours. Remaining non-specifically bound ligand protein is removed from the fiber membranes by successively washing the fibers in (i) 0.1 M TRIS 0.5 M NaCl pH 8.5, (ii) 0.1 M glycine-HCl 1 M NaCl pH 3.0 and (iii) phosphate buffered saline pH 8.0 with 0.02% sodium azide (PBSA pH 8). The fiber membranes are washed three times for five minutes with each of the above solutions. Solutions (i) and (ii) each contain 0.01% monooleate (TWEEN 80). The fiber membranes are stored at 4° C. in the final wash buffer.

6.1.3. Determination of The Amount Of Immobilized Protein G

The membrane fiber samples prepared above are analyzed for the presence of immobilized ligand protein using a commercial protein determination. (BCA Protein Assay Reagent Catalogue No. 23225G from Pierce Chemical Co.) A 2-cm segment of each membrane fiber sample is incubated for 30 minutes at 60° C. with 3 mL of the assay reagent prepared in accordance with the manufacturer's instructions provided with the assay reagent. A standard curve is prepared under the same conditions using the original protein G stock solution. The assay mixtures containing the membrane fiber samples are read (along with the Protein G standards) in a spectrophotometer at 570 nm and the amount of immobilized Protein G ligand per mL of each fiber membrane sample is calculated using linear regression analysis based on a matrix volume ("MV") of 20 μL per 2-cm segment. Results are presented below:

| Sample | mg EDC per mg Protein G ligand | Protein G Immobilized (mg/mL MV) |
|---|---|---|
| 1 | 0 | 1.83 |
| 2 | 0.02 | 2.15 |
| 3 | 0.05 | 2.29 |
| 4 | 0.1 | 2.71 |

6.1.4. Determination of Target Protein Binding Capacity

The membrane fiber samples prepared above are evaluated for their ability to bind target human IgG (hIgG) protein. Accordingly, three 2-cm pieces of each of the membrane fiber samples treated above are incubated in 4 mL of a 5 mg/ml solution of intravenous hIgG at room temperature. This solution is prepared by reconstituting 2500 mg of hIgG, available under the tradename IVEEGAM from Melville Biologics Co., with 50 mL water, and diluting the resulting solution tenfold with PBSA pH 8 on a rotary shaker for two hours at room temperature. Unbound hIgG is removed by washing the membrane fiber samples three times for 5 minutes each with 5 mL of PBSA, pH 8. The bound hIgG on the fiber membranes is eluted by incubating the fiber membranes with 2 mL of 0.1 M citrate pH 2.5 for two hours. The amount of hIgG eluted is determined by measuring the absorbance of the eluate at 280 nm in a spectrophotometer and determining the concentration based on an absorbance of 1.4 for a 1 mg/mL hIgG solution. The hIgG binding capacities of the activated membranes, together with values of mg hIgG per mg immobilized Protein G (which measures the biological function of the immobilized Protein G ligand) are presented below:

| Sample | mg EDC per mg Protein G | Immobilized Protein G Ligand (mg/mL MV) | hIgG binding capacity (mg/mL MV) | mg hIgG per mg Protein G ligand |
|---|---|---|---|---|
| 1 | 0 | 1.83 | 5.0 | 2.8 |
| 2 | 0.02 | 2.15 | 6.0 | 2.8 |
| 3 | 0.05 | 2.29 | 6.4 | 2.8 |
| 4 | 0.1 | 2.71 | 6.8 | 2.5 |

6.2. EXAMPLE 2

Four 0.25 mL samples of a 20 mg/ml solution of Protein G in water are pH adjusted by addition of 0.05 mL of the 0.6 M MES buffer employed in Example 1. A 20 mg/ml EDC solution in 0.1 M MES buffer prepared as in Example 1 is added to each sample in varying amounts as shown below:

| Sample | μL EDC added | mg EDC per mg Protein G |
|---|---|---|
| 1 | 0 | 0 |
| 2 | 2.5 | 0.01 |
| 3 | 6.25 | 0.025 |
| 4 | 12.5 | 0.05 |

The samples are incubated for two hours at room temperature, diluted with 2.7 mL of the 0.1 M MES buffer and dialyzed against two charges of 2 L 0.01 M sodium bicarbonate at 4° C.

One milliliter dialyzed portions are diluted with 3 mL of 0.01 M sodium bicarbonate at pH 9, and are contacted with five 2-cm pieces of FMP activated PES fiber as described in Example 1. The resulting fiber membrane samples are analyzed to determine the respective amounts of immobilized Protein G ligand and the hIgG binding capacities of the membranes as in Example 1. Results are listed below:

| Sample | mg EDC per mg Protein G | Protein G Ligand Immobilized (mg/mL MV) | hIgG binding capacity (mg/mL MV) | mg hIgG bound per mg Protein G |
|---|---|---|---|---|
| 1 | 0 | 1.45 | 4.7 | 3.2 |
| 2 | 0.01 | 1.67 | 6.3 | 3.8 |
| 3 | 0.025 | 1.97 | 6.9 | 3.5 |
| 4 | 0.05 | 2.26 | 7.3 | 3.2 |

6.3. EXAMPLE 3

A 20 mg/ml solution of Protein G ligand in 0.1 M MES buffer of pH 4.5 is prepared by combining 2.5 mL of 40 mg/ml Protein G stock, 0.83 mL of the 0.6 M MES buffer employed in Example 1 and 1.67 mL water. A solution of poly-lysine hydrobromide (MW 30,000–70,000; Sigma) is prepared by dissolving 35 mg of poly-lysine hydrobromide in 1.0 ml of the 0.1 M MES buffer. These reagents are combined with the 0.1 M MES buffer and a 20 mg/ml EDC solution in 0.1 M MES buffer in the proportions listed below:

| Sample | mL Protein G solution | mL 0.1M MES buffer | mL poly-L-lysine | mL EDC solution |
|---|---|---|---|---|
| 1 | 0.2 | 0.2 | 0 | 0 |
| 2 | 0.2 | 0.2 | 0.04 | 0 |
| 3 | 0.2 | 0.2 | 0.02 | 0.02 |
| 4 | 0.2 | 0.2 | 0.04 | 0.02 |

The solution samples are incubated for 2 hours at room temperature and diluted with 1.6 mL of 0.02 M sodium bicarbonate. SDS-PAGE analysis indicated that the reaction mixtures in samples 1 and 2 contained essentially unaltered Protein G. The majority of the protein in samples 3 and 4, however, remained at the top of the gel, consistent with a molecular weight in excess of 180,000.

One-milliliter portions of each solution sample are combined with 3 mL of 0.03 M sodium bicarbonate and contacted with FMP-activated membrane PES fiber as described in the previous examples.

The membrane fiber samples are analyzed as in Example 1 to determine the amounts of immobilized Protein G and the hIgG binding capacities. Results are listed below:

| Sample | mg EDC per mg Protein G | mg poly-lys per mg Protein G | Protein G Immobilized (mg/mL MV) | hIgG capacity (mg/mL MV) | mg hIgG per mg Protein G |
|---|---|---|---|---|---|
| 1 | 0 | 0 | 1.39 | 4.9 | 3.5 |
| 2 | 0 | 0.2 | 1.46 | 5.2 | 3.6 |
| 3 | 0.1 | 0.1 | 5.64 | 17.5 | 3.1 |
| 4 | 0.1 | 0.2 | 4.12 | 14.5 | 3.5 |

6.4. EXAMPLE 4

A 10 mg/ml solution of recombinant Protein A (rPA) from Repligen Inc. is prepared by reconstituting 500 mg of Protein A with 50 mL distilled water. To 1.0 mL of this solution is added 0.2 mL of the 0.6 M MES buffer of Example 1 followed by 0.05 mL of the 20 mg/ml EDC solution in 0.1 M MES buffer of Example 3. The mixture is incubated for two hours at room temperature and then diluted with 0.03 M sodium bicarbonate to yield a protein concentration of 0.6 mg/mL. SDS PAGE analysis indicated that a majority of the rPA had been converted to products ranging from 90,000 to more than 180,000 in molecular weight.

Five pieces of FMP-activated membrane PES fiber prepared as in Example 1 are contacted with 4-ml samples of the Protein A solution for 16 hours at 30° C. Identical fiber membranes also are incubated as in Example 1 with a sample of rPA that had not been treated with EDC. After incubation, residual FMP groups on the membrane fibers are deactivated by 1 hour treatment with 0.1 M NaOH. The fibers are washed to remove unbound Protein A using the procedure described in Example 1.

Fiber samples are analyzed for immobilized rPA using the BCA Assay Reagent of Example 1 with rPA as the standard and then are assayed for hIgG binding capacity as in Example 1. Results are listed below:

| Sample | mg EDC per mg rPA | rPA Immobilized (mg/mL MV) | hIgG capacity (mg/mL MV) | mg hIgG per mg rPA |
|---|---|---|---|---|
| Control | 0 | 3.26 | 12.4 | 3.80 |
| EDC | 0.1 | 5.91 | 22.4 | 3.79 |

6.5. EXAMPLE 5

A 25 mg/ml solution of the rpA of Example 4 is prepared by reconstituting 500 mg of Protein A with 20 ml of distilled water. The pH is adjusted by addition of 0.2 volumes of the 0.6 M MES buffer of Example 1. To this mixture is added a sufficient volume of a 50 mg/ml aqueous EDC solution in the 0.1 M MES buffer solution of example 3 to yield a final EDC concentration of 2 mg/ml. The resulting solution is mixed and maintained at room temperature for three hours. Four volumes of 0.02 M aqueous $Na_2CO_3$ are combined with the resulting solution and are diluted with 0.03 M $NaHCO_3$ to yield a final EDC-modified Protein A mixture with a Protein A concentration of 0.6 mg/ml.

Three hundred milliliters of the EDC-modified Protein A mixture obtained above are applied to FMP-activated hollow fiber PES membranes contained within a 10 mL matrix volume (nominal) affinity membrane module prepared as in Example 1. The mixture is convected through the fibers using a peristaltic pump at 30° C. for a period of approximately 16 hours. The remaining fluid is drained from the module and the fibers are contacted successively with 0.1 M NaOH followed by the wash buffers described in Example 1.

The static hIgG capacity of each module is determined by connecting the module to a fluid delivery system and passing 1600 mL of a 0.2 mg/ml hIgG solution in PBSA through the fibers at a flow rate of approximately 50 mL/min. Residual unbound hIgG is displaced from the module and surrounding tubing with PBSA, and the bound hIgG is eluted by pumping 0.1 M citrate pH 3 through the fibers. The amount of eluted hIgG is determined by measuring the absorbance at 280 nm of the eluate in a DU-64 Beckman Instruments spectrophotometer. The capacity of each module is calculated from absorbance of 1.4 optical density units per 1 mg/ml hIgG solution based on the amount of hIgG eluted and the nominal matrix volume of the module. In a comparison experiment, 300 mL of unmodified Protein A at the same concentration is contacted with an FMP-activated affinity module in the same manner. Results are listed below:

| Protein A | IgG eluted (mg) | IgG capacity (mg/ml MV) |
|---|---|---|
| Unmodified | 77.7 | 7.8 |
| EDC-modified | 165 | 16.5 |

6.6. EXAMPLE 6

1.5 grams of Glyceryl CPG beads ($\approx 100$ μm diameter 3000A pore size) from CPG, Inc. (Cat. #GLY03000B) are wetted out with 25 mL $H_2O$ under vacuum. The water is decanted and the beads are resuspended in 30 mL 0.1 M $Na_2IO_4$ in water to generate aldehyde functionalities on the beads. The beads are allowed to react with the $Na_2IO_4$ at room temperature for three hours. The activated beads bearing the aldehyde functionalities are washed five times with 50 mL water and then twice with 30 mL 0.1 M $NaHCO_3$ 0.15 M NaCl pH 9.0.

To 1.0 mL of the activated beads in a 15 mL centrifuge tube is added 1.5 mL 0.1 M $NaHCO_3$ 0.15 M NaCl pH 9.0 and 0.5 mL of a Protein A-EDC reaction mixture. The protein A-EDC reaction mixture is prepared by mixing the following solutions: 50 mg Protein A in 2.0 mL water; 0.4 mL 0.6 M MES pH 4.5; and 0.25 mL 20 mg/mL EDC in 0.1 M MES pH 4.5 and incubating at room temperature for three hours. A control sample is prepared using 0.5 mL of the monomeric Protein A solution prepared as described above except that 0.25 mL 0.1 M MES pH 4.5 is used instead of the EDC solution.

The tube containing the buffer, activated beads, and Protein A-EDC reaction mixture is incubated overnight at room temperature.

Residual aldehydes are capped and Schiff base linkages reduced by adding 45 mg glycine and 19 mg $NaCNBH_3$ to each tube. The tubes are incubated four hours and then decanted. The beads are washed with 10 mL 0.03 M $NaHCO_3$ and then four times with alternating 0.1 M Tris 0.5 M NaCl 0.01% Tween 80 pH 9.0 and 0.1 M glycine 1.0 M NaCl 0.01% Tween 80 pH 2.5. The beads are washed four times with PBSA pH 8.0 and stored in 5 mL PBSA pH 8.0.

6.7. EXAMPLE 7

CNBr-activated agarose (SEPHAROSE) gel is obtained from Pharmacia (Cat #17-0430-01). 2.5 grams of lyophilized gel are allowed to swell for 30 minutes in 50 mL 1 mM HCl. The swollen gel is washed 4 times with 50 mL 1 mM HCl.

A sufficient amount of the resulting gel suspension is transferred to a 15 mL centrifuge tube to yield 1.0 mL packed gel in the tube. Excess liquid is removed and the gel resuspended in 0.25 M $NaHCO_3$ 0.5 M NaCl pH 9.0 and then centrifuged and decanted. 0.5 mL of the Protein A-EDC reaction mixture described above in Example 6 is combined with 1.5 mL 0.25 M $NaHCO_3$ 0.5 M NaCl pH 9.0 and is added to the tube containing the activated gel. A second control tube is prepared in the same fashion except that the monomeric Protein A (no EDC) reaction mixture of Example 6 is used.

Both tubes are incubated overnight at room temperature on an end-over-end mixer. The gel samples are washed with 0.03 M $NaHCO_3$, 0.1 M Tris 0.5 M NaCl 0.01% monooleate (TWEEN 80) pH 9.0, 0.1 M glycine 1.0 M NaCl 0.01% monooleate (TWEEN 80) pH 2.5 and PBSA pH 8.0 in the sequence described above in Example 6.

6.8. EXAMPLE 8

Epoxy-activated polymer-silica composite beads (40–100 μm diameter, 110 μmole epoxy groups per mL) are prepared. Porous silica beads (1 $cm^3$/g porous volume: 1200–1500 Å pore diameter) are treated with a monomer solution to fill the pores of the beads. The monomer solution is obtained by combining 1 gram N,N'-methylene-bis-acrylamide (MBA) in 50 mL water, 3 mL of 50% methacrylamidopropyl trimethyl ammonium chloride (MAPTAC) in water, and 10 mL glycidylmethacrylate in 40 mL dimethysulfoxide (DMSO). To this mixture is added 1 gram ammonium persulfate with stirring.

While shaking, the solution of monomers is added dropwise to 100 g of porous silica (40 to 100 μm diameters, 1000 to 1500 Å pore diameter, 20 to 35 $m^2$/g surface area and 1 $cm^3$/g porous volume).

After 30 minutes of shaking, 250 ml of paraffin oil is added, the agitated suspension is heated at 60° to 70° C. and then 1 ml of N,N,N',N'-tetramethylethylene diamine is added.

After a few minutes, the exothermic polymerization reaction occurs. The obtained composite material is separated by filtration, and is washed with a chlorinated solvent to remove excess paraffin oil. It is then washed with water several times and then dried under vacuum (T<30°) after a final wash with ethanol.

1.5 grams of the activated beads are wetted out with 30 mL 1 M potassium phosphate pH 7.4 under vacuum. A sufficient amount of the resulting suspension is transferred to a 15 mL centrifuge tube to yield 1.0 mL packed gel in the tube. Excess liquid is decanted. 0.5 mL of the Protein A-EDC reaction mixture of Example 6 is combined with 1.5 mL 1 M potassium phosphate pH 7.4 and added to the tube containing the activated beads. A second control tube is prepared in the same manner except that the monomeric Protein A (no EDC) reaction mixture of Example 6 is used.

Both tubes are incubated overnight at room temperature on an end-over-end mixer. Residual epoxy groups are capped by 4 hour incubation with 0.2 M μ-mercaptoethanol. The samples are then washed with 0.03 M NaHCO$_3$, 0.1 M Tris 0.5 M NaCl 0.01% monooleate (TWEEN 80) 9.0, 0.1 M glycine 1.0 M NaCl 0.01% monooleate (TWEEN 80) pH 2.5 and PBSA pH 8.0 in the sequence described above in Example 6.

6.9. EXAMPLE 9

Glyceryl CPG beads are activated with FMP in a manner similar to that described in Example 1. The resulting FMP-activated CPG suspension is transferred to a 15 mL centrifuge tube to yield 1.0 mL packed gel in the tube. The beads are washed with 12 mL 0.03 M NaHCO$_3$ pH 9.0. Excess liquid is decanted. 0.5 mL of the Protein A-EDC reaction mixture of Example 6 is combined with 1.5 mL 0.03 M NaHCO$_3$ pH 9.0 and added to the tube containing the activated beads. A second control tube is prepared in the same manner except that the monomeric Protein A (no EDC) reaction mixture of Example 6 is used.

Both tubes are incubated overnight at room temperature on an end-over-end mixer. Residual FMP-activated groups are capped by 4 hour incubation with 0.2 M β-mercaptoethanol. The gel samples are then washed with 0.03 M NaHCO$_3$, 0.1 M Tris 0.5 M NaCl 0.01% monooleate (TWEEN 80) 9.0, 0.1 M glycine 1.0 M NaCl 0.01% monooleate (TWEEN 80) pH 2.5 and PBS 0.02% Na azide pH 8.0 in the sequence described above for Example 6.

6.10. EXAMPLE 10

"Passivated" silica beads are prepared. Porous silica beads are functionalized with the following solutions of monomers in 100 ml of distilled water: 10 g tris-hydroxymethyl-methyl-methacrylamide (THMMA), 1.5 g MAPTAC, and 2.0 g MBA.

While shaking, the solution of monomers is added dropwise to 100 g of porous silica (40 to 100 μm diameters, 1000 to 1500 Å pore diameter, 20 to 35 m$^2$/g surface area and 1 cm$^3$/g porous volume).

After 30 minutes of shaking, 250 ml of paraffin oil is added, the agitated suspension is heated at 60 to 70° C. and then 1 ml of N,N,N',N'-tetramethylethylene diamine is added.

After a few minutes, the exothermic polymerization reaction occurs. The resin is then separated by a chlorinated solvent and dried at room temperature. Lastly, the resin is washed extensively with dilute hydrochloric acid, dilute sodium hydroxide and 1 M sodium chloride.

The resulting beads are activated with FMP in accordance with the procedure of Example 9. A sufficient amount of the resulting FMP-activated suspension is transferred to a 15 mL centrifuge tube to yield 1.0 mL packed gel in the tube. The beads are washed with 12 mL 0.03 M NaHCO$_3$ pH 9.0. Excess liquid is decanted. 0.5 mL of the Protein A-EDC reaction mixture of Example 6 is combined with 1.5 mL 0.03 M NaHCO$_3$ pH 9.0 and added to the tube containing the activated beads. A second control tube is prepared in the same fashion except that the monomeric Protein A (no EDC) reaction mixture of Example 6 is used.

Both tubes are incubated overnight at room temperature on an end-over-end mixer. Residual FMP-activated groups are capped by 1 hour incubation with 0.1 M NaOH. The gel samples are washed with 0.03 M NaHCO$_3$, 0.1 M Tris 0.5 M NaCl 0.01% monooleate (TWEEN 80) pH 9.0, 0.1 M glycine 1.0 M NaCl 0.01% monooleate (TWEEN 80) pH 2.5 and PBSA pH 8.0 in the sequence described above for Example 6.

The amounts of Protein A attached to the gel suspensions of Examples 6–10 are evaluated by BCA reagent analysis. In this procedure, 100 uL of each of the gel suspensions (containing 20 uL gel) produced in Examples 6–10 are combined with 3 mL of the BCA reagent of Example 1 and incubated for 30 minutes at 60° C. with periodic agitation. The samples are cooled and 100 uL of each supernatant is transferred to a 96 well microtitre plate. The plate is read at 570 nm using a microtitre plate reader. Values for the gel supernatants are compared with those of Protein A standards prepared and analyzed in parallel. The amount of Protein A immobilized is determined using linear regression analysis. Results are shown in FIG. 1.

Figure 2:
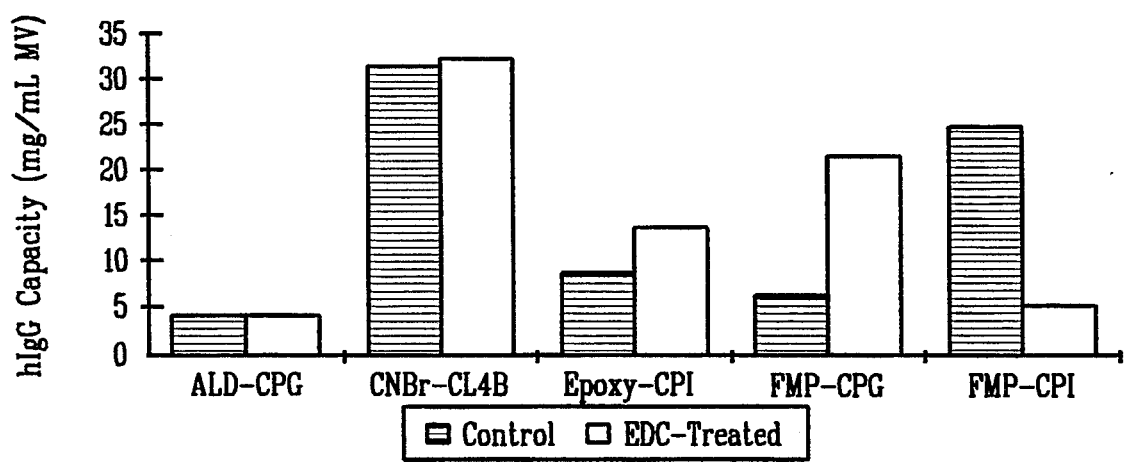
FIG. 2 shows the effect of EDC treatment of Protein A on human Immunoglobulin G (hIgG) protein binding capacity.

The respective hIgG binding capacities of the activated materials of Examples 6–10 are evaluated by mixing 0.5 mL of each gel suspension (containing 0.1 mL beads) with 4.0 mL of a 5 mg/mL solution of IVEEGAM hIgG in PBSA pH 8.0. Samples are incubated on a rocker for two hours. The beads are washed three times with 10 mL PBSA pH 8.0 and eluted with 0.1 M sodium citrate pH 2.5 for 2 hours. The amount of hIgG bound and eluted is determined by measuring the absorbance of the eluates at 280 nm in a spectrophotometer. Results are shown in FIG. 2.

It can be observed that in Example 10 the apparent biological activity of the ligand is significantly reduced as a result of modification with EDC. While not wishing to be limited by theory, it is believed that this phenomenon may stem from occlusion of the pores of the bead due to excessive monomer concentration during the "passivation" process.

It should be apparent to those skilled in the art that other high-capacity affinity supports, methods of making same, and methods of utilizing same not specifically disclosed in the instant specification are, nevertheless, contemplated thereby. Such other supports and methods are considered to be within the scope and spirit of the present invention. Hence, the invention should not be limited by the description of the specific embodiments disclosed herein but only by the following claims.

What is claimed is:

1. An affinity support for binding a target compound during affinity separations comprising:
   (a) a solid support selected from the group consisting of porous particles, nonporous particles, and porous membranes wherein said solid support comprises a material selected from the group consisting of agarose, polyethersulfone, polystyrene, silica, celluloses, polytrisacryl, poly-meta-trisacryl, controlled pore glass, dextran, polyamides, polyacrylamide, hydroxyalkylmethacrylate gels, polyacrylamide/agarose gels, ethylene copolymers, diol-bonded silica, copolymers of methacrylamide, methylene bis-methacrylamide, glycidyl-methacrylate, allyl-glycidyl-ether, polyethersulfone coated with hydroxyethylcellulose, and polymer-silica composites; and
   (b) a modified ligand immobilized on the surface of said solid support, said modified ligand comprising a plurality of ligand molecules selected from the group consisting of Protein A, Protein G, and hybrids thereof and covalently bound to one another by the action of a condensation or crosslinking reagent selected from the group consisting of carbodiimides, dialdehydes, bifunctional imidoesters, and 2-ethyl-5-phenylisoxazolium-3'-sulfonate prior to immobilization of said modified ligand on said support, such that said modified ligand (i) has a molecular weight that is greater than that of an individual ligand molecule, and (ii) exhibits a selective and reversible binding affinity for said target compound.

2. The affinity support of claim 1 in which said particle or membrane comprises a material selected from the group consisting of a polymer-silica composite and a polyethersulfone coated with hydroxyethylcellulose.

3. The affinity support of claim 1 in which the surface of said solid support had been activated with an activation agent prior to immobilization of said modified ligand.

4. The affinity support of claim 3 in which the surface of said support is activated with epoxy, fluoro-methylpyridinium p-toluenesulfonate, cyanogen bromide, triazine, carbonyl diimidazole, N-hydroxysuccinimide, aldehyde or hydrazide functionalities.

5. The affinity support of claim 1 in which said modified ligand is an oligomer of two or more proteins selected from the group consisting of Protein A, Protein G, and hybrids thereof.

6. An affinity support having an increased capacity for binding a target compound during affinity separations comprising:
(a) a solid support material comprising a polyethersulfone and having a surface (i) coated with hydroxyethylcellulose, and (ii) activated with fluoromethylpyridinium p-toluenesulfonate; and
(b) a modified ligand immobilized on the surface of said solid support material, said modified ligand comprising a plurality of ligand molecules selected from the group consisting of Protein A. Protein G and hybrids thereof and covalently bound to one another prior to immobilization of said modified ligand on said support by the action of ethyl-3-(3-dimethylaminopropyl)carbodiimide, such that said modified ligand (i) has a molecular weight that is greater than that of an individual ligand molecule, and (ii) exhibits a selective and reversible binding affinity for said target compound.

7. A method of making an affinity support for binding a target compound during affinity separations of the target compound from a mixture of compounds, comprising chemically modifying ligand molecules selected from the group consisting of Protein A, Protein G and hybrids thereof by the action of a condensation or crosslinking reagent selected from the group consisting of carbodiimides, dialdehydes, bifunctional imidoesters, and 2-ethyl-5-phenylisoxazolium-3'-sulfonate to form a modified ligand comprising a plurality of said ligand molecules covalently bound to one another, and subsequently immobilizing the modified ligand onto the surface of a solid support selected from the group consisting of porous particles, non-porous particles, and porous membranes wherein said solid support comprises a material selected from the group consisting of agarose, polyethersulfone, polystyrene, silica, celluloses, polytrisacryl, poly-meta-trisacryl, controlled pore glass, dextran, polyamides, polyacrylamide, hydroxyalkylmethacrylate gels, polyacrylamide/agarose gels, ethylene copolymers, diol-bonded silica, copolymers of methacrylamide, methylene bis-methacrylamide, glycidylmethacrylate, allyl-glycidyl-ether, polyethersulfone coated with hydroxyethylcellulose, and polymer-silica composites, such that said modified ligand (i) has a molecular weight that is greater than that of ann individual ligand molecule, and (ii) exhibits a selective and reversible binding affinity for said target compound.

8. The method of claim 7 in which the immobilization of said modified ligand is effected by adsorption thereof onto said solid support.

9. The method of claim 7 in which the immobilization of said modified ligand is effected by activating the solid support with an activation agent and contacting said modified ligand with the solid support.

10. The method of claim 9 in which the solid support is activated with epoxy, fluoro-methylpyridinium p-toluenesulfonate, cyanogen bromide, triazine, carbonyl diimidazole, N-hydroxysuccinimide, aldehyde or hydrazide functionalities.

11. The method of claim 7 in which the particle or membrane comprises a material selected from the group consisting of a polymer-silica composite and a polyethersulfone coated with hydroxyethylcellulose.

12. A method of making an affinity support having an increased capacity for binding a target compound during affinity separations of the target compound from a mixture of compounds, comprising chemically modifying ligand molecules selected from the group consisting of Protein A, Protein G and hybrids thereof by treating said ligand moles with ethyl-3-(3-dimethylaminopropyl)-carbodiimide to form a modified ligand comprising a plurality of said ligand molecules covalently bound to one another, activating the surface of a polyethersulfone solid support material coated with hydroxyethylcellulose by treating said solid support material with fluoro-methylpyridinium p-toluenesulfonate, and subsequently immobilizing the modified ligand onto the surface of the activated solid support material, such that said modified ligand (i) has a molecular weight that is greater than that of an individual ligand molecule, and (ii) exhibits a selective and reversible binding affinity for said target compound.

13. A method of performing affinity separations of a target compound to be separated from a mixture of compounds, comprising:
(a) contacting a mixture of compounds with an affinity support formed by
(i) chemically treating ligand molecules selected from the group consisting of Protein A, Protein G and hybrids thereof with a condensation or crosslinking reagent selected from the group consisting of carbodiimides, dialdehydes, bifunctional imidoesters, and 2-ethyl-5-phenylisoxazolium-3'-sulfonate to form a modified ligand comprising a plurality of said ligand molecules covalently bound to one another, and
(ii) subsequently immobilizing the modified ligand onto the surface of a solid support selected from the group consisting of porous particles, nonporous particles and porous membranes wherein said solid support comprises a material selected from the group consisting of agarose, polyethersulfone, polystyrene, silica, celluloses, polytrisacryl, poly-meta-trisacryl, controlled pore glass, dextran, polyamides, polyacrylamide, hydroxyalkylmethacrylate gels, polyacrylamide/agarose gels, ethylene copolymers, diol-bonded silica, copolymers of methacrylamide, methylene bis-methacrylamide, glycidyl-methacrylate, allyl-glycidyl-ether, polyethersulfone coated with hydroxyethylcellulose, and polymer-silica composites, such that said modified ligand has a molecular weight that is greater than that of an individual ligand molecule, and exhibits a selective and reversible binding affinity for said target compound; and (b) maintaining contact between the mixture and the affinity support for a time sufficient to selectively and reversibly bind the target compound to the immobilized modified ligand, thereby separating the target compound from the mixture.

14. The method of claim 13 in which the target compound is IgA, IgG, IgM or mixtures thereof.

15. The affinity support of claim 1 in which said reagent is 1-ethyl-3-(3-dimethylaminopropyl)-carbodiimide.

16. The method of claim 7 in which said reagent is 1-ethyl-3-(3-dimethylaminopropyl)-carbodiimide.

17. The method of claim 13 in which said ligand molecules are chemically treated with 1-ethyl-3-(3-dimethylaminopropyl)-carbodiimide to form said modified ligand.

18. The affinity support of claim 1 wherein said condensation or crosslinking reagent is selected from the group consisting of carbodiimides and 2-ethyl-5-phenylisoxazolium-3'-sulfonate.

19. The method as claimed in claim 7 wherein said condensation or crosslinking reagent is selected from the group consisting of carbodiimides and 2-ethyl-5-phenylisoxazolium-3'-sulfonate.

20. The method as claimed in claim 13 wherein said condensation or crosslinking reagent is selected from the group consisting of carbodiimides and 2-ethyl-5-phenylisoxazolium-3'-sulfonate.

* * * * *